United States Patent
Haartsen et al.

(10) Patent No.: US 9,072,464 B2
(45) Date of Patent: Jul. 7, 2015

(54) THERMAL FLOW SENSOR INTEGRATED CIRCUIT WITH LOW RESPONSE TIME AND HIGH SENSITIVITY

(75) Inventors: Jaap Roger Haartsen, Eindhoven (NL); Ronald Dekker, Eindhoven (NL); Pascal De Graaf, Eindhoven (NL); Nicolaas Johannes Anthonius Van Veen, Eindhoven (NL); Alphonsus Tarcisius Jozef Maria Schipper, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 462 days.

(21) Appl. No.: 13/379,226

(22) PCT Filed: Jul. 16, 2010

(86) PCT No.: PCT/IB2010/053253
§ 371 (c)(1),
(2), (4) Date: Dec. 19, 2011

(87) PCT Pub. No.: WO2011/010260
PCT Pub. Date: Jan. 27, 2011

(65) Prior Publication Data
US 2012/0103085 A1 May 3, 2012

(30) Foreign Application Priority Data
Jul. 22, 2009 (EP) .................................... 09166078

(51) Int. Cl.
*G01F 1/68* (2006.01)
*A61B 5/11* (2006.01)
(Continued)

(52) U.S. Cl.
CPC ......... *A61B 5/1117* (2013.01); *Y10T 29/49128* (2015.01); *Y10T 29/49117* (2015.01); *A61B 5/681* (2013.01); *A61B 5/6831* (2013.01);
(Continued)

(58) Field of Classification Search
None
See application file for complete search history.

(56) References Cited

U.S. PATENT DOCUMENTS 4,940,945 A * 7/1990 Littlejohn et al. ............ 324/438
5,258,781 A * 11/1993 John ................................ 347/63
(Continued)

FOREIGN PATENT DOCUMENTS

CN 101115351 A 1/2008
JP 11317474 A 11/1999
(Continued)

OTHER PUBLICATIONS

Kim et al, "Measurement of Flow Direction and Velocity Using a Micromachined Flow Sensor", Sensors and Actuators A Physical, vol. 114, 2004, pp. 312-318.

*Primary Examiner* — Harshad R Patel (57) ABSTRACT

A thermal flow sensor integrated circuit for sensing flow in a channel based on temperature measurements, the integrated circuit having a temperature sensing element (30) on a front side of the integrated circuit arranged to face the channel, and a bond pad (60, 200) coupled electrically to the temperature sensing element, for making electrical contact off the integrated circuit, the bond pad being arranged to face away from the channel. By having the bond pad facing away from the channel, the space needed for the bond pad and any connections to it need not extend beyond the temperature sensing element and get in the way of the channel. Hence the temperature sensing element can be located closer to the channel or in the channel to enable measurements with better response time and sensitivity.

15 Claims, 10 Drawing Sheets

(51) Int. Cl.
    *A61B 5/00*      (2006.01)
    *A61M 15/00*     (2006.01)
    *G01P 5/10*      (2006.01)
    *G01P 5/12*      (2006.01)
    *G01P 13/00*     (2006.01)
    *G08B 21/04*     (2006.01)
    *A61M 5/168*     (2006.01)
    *A61M 16/00*     (2006.01)

(52) U.S. Cl.
    CPC . *A61B2562/0219* (2013.01); *A61B 2562/0271* (2013.01); *A61M 5/16886* (2013.01); *A61M 15/00* (2013.01); *A61M 2016/0021* (2013.01); *A61M 2205/332* (2013.01); *A61M 2205/3334* (2013.01); *A61M 2205/3368* (2013.01); *A61M 2205/3375* (2013.01); *G01P 5/10* (2013.01); *G01P 5/12* (2013.01); *G01P 13/006* (2013.01); *G08B 21/0446* (2013.01)

(56) References Cited

U.S. PATENT DOCUMENTS

| | | | |
|---|---|---|---|
| 5,515,714 A * | 5/1996 | Sultan et al. | 73/25.01 |
| 5,739,591 A * | 4/1998 | Dekker et al. | 257/780 |
| 6,107,109 A | 8/2000 | Akram et al. | |
| 6,353,262 B1 | 3/2002 | Honda | |
| 6,746,932 B2 | 6/2004 | Pannek | |
| 7,255,001 B1 | 8/2007 | Davis et al. | |
| 7,264,617 B2 * | 9/2007 | Freeman | 604/890.1 |
| 2002/0017132 A1 * | 2/2002 | McNie et al. | 73/504.02 |
| 2004/0018712 A1 | 1/2004 | Plas et al. | |
| 2005/0205136 A1 * | 9/2005 | Freeman | 137/554 |
| 2006/0131736 A1 * | 6/2006 | Jansman et al. | 257/712 |
| 2007/0227260 A1 | 10/2007 | Ike et al. | |
| 2007/0251292 A1 | 11/2007 | Beck et al. | |
| 2008/0047339 A1 | 2/2008 | Hasebe | |
| 2008/0210001 A1 * | 9/2008 | Kanne | 73/204.17 |
| 2009/0229370 A1 * | 9/2009 | Fujii et al. | 73/780 |
| 2009/0308177 A1 * | 12/2009 | Lammerink et al. | 73/861.355 |
| 2010/0242591 A1 * | 9/2010 | Nakano et al. | 73/204.26 |
| 2010/0294024 A1 * | 11/2010 | Kumar et al. | 73/38 |
| 2011/0154885 A1 * | 6/2011 | Nakano et al. | 73/25.03 |
| 2012/0109575 A1 * | 5/2012 | Balbus et al. | 702/141 |
| 2013/0213129 A1 * | 8/2013 | Kumar et al. | 73/152.47 |

FOREIGN PATENT DOCUMENTS

| | | |
|---|---|---|
| JP | 2007212199 A | 8/2007 |
| WO | 03063258 A1 | 7/2003 |

* cited by examiner

THERMAL FLOW SENSOR INTEGRATED CIRCUIT WITH LOW RESPONSE TIME AND HIGH SENSITIVITY

FIELD OF THE INVENTION

This invention relates to sensor integrated circuits for sensing flow rate, to systems incorporating such integrated circuits, and to methods of manufacturing and operating such integrated circuits and such systems.

BACKGROUND OF THE INVENTION

US-A 20070251292 shows a flip integrated circuit flow sensor which has temperature sensors and a heater on top of a substrate, and has a channel for the fluid in the bottom of the substrate, to bring the fluid closer to the sensor. It is also known from U.S. Pat. No. 6,746,932 to provide an area of porous silicon in a substrate to provide better thermal insulation of a temperature sensor on the substrate, so that the sensor is more sensitive to temperature above the substrate.

SUMMARY OF THE INVENTION

An object of the invention is to provide alternative sensors and sensor integrated circuits for sensing flow rate, to systems incorporating such sensors or sensor integrated circuits, and to methods of manufacturing and operating such sensors or sensor integrated circuits and such systems. According to a first aspect, the invention provides thermal flow sensor device. This device comprises a thermal flow sensor integrated circuit or Integrated Circuit (IC) thermal flow sensor including an integrated circuit for sensing flow in a fluid channel based on temperature measurements, the integrated circuit having an electrically driven thermal element, e.g. a temperature sensing element on a front side of the integrated circuit to face the fluid channel, and a bond pad coupled electrically to the electrically driven thermal element, e.g. the temperature sensing element, for making electrical contact with the integrated circuit, the bond pad being arranged to face away from the front side to be accessible for contact from a backside of the integrated circuit.

By having the bond pad accessible from the backside of the integrated circuit, facing away from the fluid channel, the space needed for the bond pad and any connections to it need not extend beyond the electrically driven thermal element, e.g. the temperature sensing element and get in the way of the fluid channel. Hence the electrically driven thermal element, e.g. the temperature sensing element can be located closer to the fluid channel or in the fluid channel to enable better measurements.

Accurate flow rate sensing is needed in many applications. One such application is in monitoring and controlling intravenous delivery of a medication. Another such application is in nebuliser systems. Nebuliser systems are used to deliver drugs in the form of aerosols to patients with respiratory diseases. To enable accurate medication or aerosol delivery, the exact time period for the medication or aerosol release is determined based on flow sensor data. Such a flow sensor should be fast and sensitive to resolve velocity fluctuations, for instance around the turning point of inhalation to exhalation and vice versa.

Medical devices such as nebulisers may require sterilization in an autoclave, or with the use of mechanical or chemical methods. The ability to measure flow through the wall of a fluid channel makes it possible to mount the flow sensor and the electronics in a hermetically sealed part of the device, separated from the sterile environment. However, for good sensor performance in terms of sensitivity and response time the sensor should be mounted close to the fluid.

Thermal flow sensor integrated circuits are fabricated, using IC processing techniques, on top or in the upper layer of a silicon substrate. Consequently, both the sensor area and the bond pads to contact the sensor, are located at the front side of the silicon stack. Since the sensor area and the bond pads are located in the same plane it is necessary to apply a thick layer between the sensor and the fluid to protect and guide the connecting wires to a PCB or lead frame. The performance of the sensor in terms of sensitivity and response time decreases with the distance between the flow and the fluid.

In the invention a conductive layer can be provided on the front side of the thermal flow sensor device, for electrical connection between the electrically driven thermal element and the bond pad, wherein the bond pad is located on a back side of the conductive layer, facing away from the front side of the thermal flow sensor device. This has the advantage of providing an additional degree of freedom regarding the thermal conductivity of the thermal flow sensor device while providing a contact on the back side. For instance, the thickness of the conductive layer or the material comprised in the conductive layer may be employed as design variables.

The thermal flow sensor device may comprise an insulating layer for electrically insulating it from a fluid in the channel. Preferably, the insulating layer comprises poly-imide. Poly-imide has a thermal conductivity of about 0.15 W/(mK) and allows for disposition at a thickness of roughly 10 micron. As a result, thermal shunting is reduced. This advantageously increases sensitivity of the thermal flow sensor device. Furthermore the smaller thickness positively affects the response time associated with the thermal flow sensor device. In addition to that, poly-imide is easily applied by spin-coating methodologies, which methodologies advantageously circumvent the need for gluing.

The device can include a substrate, such as a semiconductor substrate. The substrate can be patterned to provide an aperture to expose the bond pad to enable contact with the bond pad through the aperture. This allows access to the bond pad while keeping a certain thickness of the substrate for mechanical strength and stability.

The substrate may also be patterned to form one or more pillars, and the bond pad can be located on a back side of the substrate on one of the pillars.

The pillars may be provided with a coating of electrical resistive material in order to increase the mechanical support of the pillars. As a result, a cross-sectional size of the pillars may be decreased while materializing sufficient mechanical strength. A reduction of the pillars' cross-sectional size decreases the size of the IC, and therefore advantageously decreases the costs of the ID. Preferably, the electrical resistive material comprises parylene since the latter material has very good step-coverage properties. Because of said excellent step-coverage properties, parylene will cover sidewalls of the pillars with almost the same rate as the horizontal surface of the substrate. An example of a suitable parylene is poly-xylylene.

The electrically driven thermal element can comprise a heating element or a temperature sensor element on a front side of the thermal flow sensor device to face the channel. Location on the front side makes the temperature sensor more sensitive.

The device can be formed as an integrated circuit. This makes a compact device that can be easily included within other equipment. The IC can be a silicon on insulator integrated circuit.

The present invention also provides an assembly comprising a printed circuit board and the thermal flow sensor device described above mounted on the printed circuit board, with the bond pad coupled to a corresponding contact on the printed circuit board.

The present invention also provides a system having a channel, the channel having a wall, the wall having a recess, and in the recess is mounted the thermal flow sensor device or the assembly described above, with the electrically driven thermal element facing the channel.

The present invention also provides a method of manufacture of a thermal flow sensor device for sensing a flow in a fluid channel based on temperature measurements, the method having the steps of:

forming an electrically driven thermal element on a front side of the thermal flow sensor device arranged to face the channel, and forming a bond pad coupled electrically to the electrically driven thermal element, for making electrical contact with the thermal flow sensor device, the bond pad being arranged to face away from the front side to be accessible for contact from a backside of the thermal flow sensor device. The back side of the conductive layer faces away from the front side of the thermal flow sensor device. These methods steps are compatible with a standard CMOS processing flow, which allows economical manufacture.

A conductive layer can be provided for electrical connection between the electrically driven thermal element and the bond pad, whereby the bond pad comprises a back side of the metal layer. When this layer is on the front side of the device it can help to improve the thermal response time along a direction parallel to the main direction of the fluid channel.

The thermal flow sensor device can have a substrate such as a semiconducting substrate, and the method can have the step of patterning the substrate to provide an aperture to expose the bond pad to enable contact with the bond pad through the aperture.

The method may also have the step of patterning the substrate to form a pillar, the step of forming the bond pad comprising forming the bond pad on the pillar.

The method may include the step of assembling the thermal flow sensor device onto a printed circuit board, and coupling the bond pad to a corresponding contact on the printed circuit board.

The thermal flow sensor device may be advantageously mounted into a recess in a wall of a channel for fluid flow.

Other aspects of the invention include sensors and sensor systems having such integrated circuits and methods of manufacturing such integrated circuits or such systems and methods of operating such sensors and sensor systems having such integrated circuits.

The present invention also provides a method of manufacture of a thermal flow sensor device, e.g. a thermal flow sensor integrated circuit for sensing flow in a fluid channel based on temperature measurements, comprising the steps of:

forming an electrically driven thermal, e.g. an element temperature sensing element on a front side of the integrated circuit arranged to face the fluid channel, and forming a bond pad coupled electrically to the electrically driven thermal element or the temperature sensing element, for making electrical contact off the integrated circuit, the bond pad being arranged to face away from the fluid channel.

The method can involve the step of forming the bond pad on a backside of a metal layer, or patterning a substrate to form an aperture, and forming the bond pad in the aperture, or patterning a substrate to form a pillar and forming the bond pad on the pillar.

Any additional features can be added, some are described in more detail below. Any of the additional features can be combined together and combined with any of the aspects, as would be apparent to those skilled in the art. Other advantages will be apparent to those skilled in the art, especially over other prior art. Numerous variations and modifications can be made without departing from the claims of the present invention. Therefore, it should be clearly understood that the form of the present invention is illustrative only and is not intended to limit the scope of the present invention.

BRIEF DESCRIPTION OF THE DRAWINGS

How the present invention may be put into effect will now be described by way of example with reference to the appended drawings, in which.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

The term "comprising", used in the claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

The present invention will be described with reference to a thermal flow sensor integrated circuit for sensing flow in a channel based on temperature measurements, the integrated circuit having:

a temperature sensing element on a front side of the integrated circuit to face the fluid channel, and a bond pad coupled electrically to the temperature sensing element, for making electrical contact off the integrated circuit, the bond pad being arranged to face away from the front side to be accessible for contact from a backside of the integrated circuit.

DETAILED DESCRIPTION OF THE EMBODIMENTS

In some of the embodiments, an Integrated Circuit (IC) processed thermal flow sensor is shown with bond pads fabricated at the backside of the sensor to enable easy mounting, and a fast and sensitive sensor response. Since the bond pads are fabricated in a post-processing step, the steps described can be compatible with mainstream IC processes such as CMOS processing, especially standard CMOS processing, thus enabling the integration of on-integrated circuit driving electronics. In another embodiment the sensor can be mounted on a printed circuit board (PCB) in a pick-and-place procedure to enable high volume, low cost production.

In some embodiments, there is a metal layer on the front side of the integrated circuit, for electrical connection between the sensing element and the bond pad, and the bond pad comprises the back side of the metal layer. This enables the bond pad to be relatively close to the sensing element to keep the structure simple and compact. An example is shown in the first embodiment described below.

In some embodiments, the integrated circuit comprises a substrate and the substrate is patterned to provide an aperture to expose the bond pad to enable contact to the bond pad through the aperture. This can help protect the contact and provide a compact structure.

In some embodiments the integrated circuit comprises a substrate and the substrate is patterned to form one or more pillars, and the bond pad is located on a back side of the substrate on one of the pillars. The pillars can provide support for the bond pad, and maintain isolation from other circuitry. An example is shown in the second embodiment described below.

In some embodiments the integrated circuit comprises a heating element on a front side of the integrated circuit to face the fluid channel. This enables a more integrated solution, although in alternative embodiments, the heating can be provided by a heater external to the integrated circuit. The external heater should be provided so that the fluid is heated sufficiently closely to the temperature sensor.

In some embodiments the integrated circuit comprises a silicon on insulator integrated circuit. This helps enable other circuit elements to be integrated. The third embodiment described below discloses this arrangement.

In some embodiments there is an assembly comprising a printed circuit board and the integrated circuit of any embodiment, mounted on the printed circuit board, with the bond pad coupled to a corresponding contact on the printed circuit board. This enables other circuit elements to be mounted on the board, as an alternative to having them integrated on the same integrated circuit, which could be less expensive or easier to manufacture. It also allows additional components to be included with the integrated circuit. An example is shown in the fourth embodiment described below.

In some embodiments, there is a system having a fluid channel for the fluid flow, the channel having a wall having a recess, and in the recess is the integrated circuit or the assembly, with the sensing element facing the channel.

The present invention also provides a method of manufacture of a thermal flow sensor integrated circuit for sensing flow in a fluid channel based on temperature measurements, which can involve the steps of:

forming an electrically driven thermal element such as a temperature sensing element on a front side of the integrated circuit arranged to face the fluid channel, and forming a bond pad coupled electrically to the electrically driven thermal element such as the temperature sensing element, for making electrical contact off the integrated circuit, the bond pad being arranged to face away from the fluid channel.

The method can involve the step of forming the bond pad on a backside of a metal layer, or patterning a substrate to form an aperture, and forming the bond pad in the aperture, or patterning a substrate to form a pillar and forming the bond pad on the pillar.

In summary, the embodiments described involve an IC processed thermal flow sensor with bond pads fabricated at the backside of the sensor. As the bond pads can be fabricated in a post-processing step, at least some embodiments are compatible with mainstream IC processes such as CMOS processing, especially standard CMOS processing, thus enabling the integration of, for example, on-integrated circuit driving electronics. In another embodiment a method to mount the sensor on a PCB in a pick-and-place procedure is shown to enable high volume, low cost production.

A thermal flow sensor typically comprises one or more heating elements and/or one or more temperature sensing elements such as resistors, transistors or thermocouples. The heating element (on integrated circuit or elsewhere) heats up the part of the fluid that is located close to the sensor. The fluid flow induces a decrease in the heater temperature and a shift in the temperature profile of the integrated circuit, which can be measured with the temperature sensing elements. Both the heater temperature as well as the shift in temperature profile can be used as a measure for the flow rate. An additional benefit of the temperature profile measurement is the ability to determine flow direction.

In embodiments of the present invention, the term "substrate" may include any underlying material or materials that may be used, or upon which a device, a circuit or an epitaxial layer may be formed. In other alternative embodiments, this "substrate" may include a semiconductor substrate such as e.g. silicon, doped silicon, a gallium arsenide (GaAs), a gallium arsenide phosphide (GaAsP), an indium phosphide (InP), a germanium (Ge), or a silicon germanium (SiGe) substrate. The "substrate" may include for example, an insulating layer such as a $SiO_2$ or a $Si_3N_4$ layer in addition to a semiconductor substrate portion. Thus, the term substrate also includes silicon-on-glass, silicon-on sapphire substrates. The term "substrate" is thus used to define generally the elements for layers that underlie a layer or portions of interest.

A first embodiment of the invention is an integrated circuit manufactured as shown in FIGS. 1 to 13, having a bond pad accessible through an aperture in the substrate.

Figure 1:
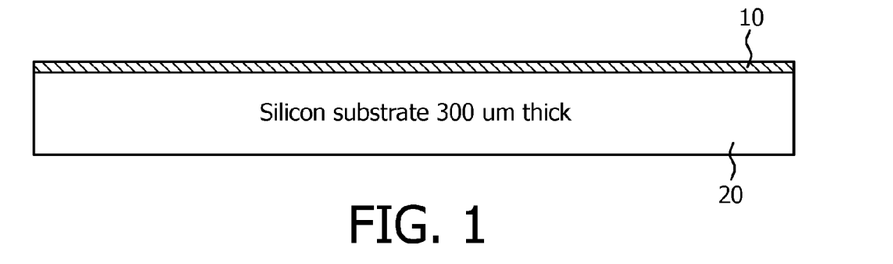
FIGS. 1 to 13 show steps in a method of manufacturing an integrated circuit according to a first embodiment, having a bond pad accessible through an aperture in the substrate.

FIG. 1 shows the starting material, in this case a semiconductor substrate such as a semiconductor wafer of which a 300 micron thick silicon substrate 20 with an insulating layer on top such as an oxide layer, e.g. a 0.5 micron thermal oxide layer 10 on top is an example. Other insulating layer thicknesses or insulating layer materials could be used such as silicon nitride. The heating elements and temperature sensing elements can be processed using standard deposition and lithography techniques (shown in FIGS. 2 to 7).

Figure 2:
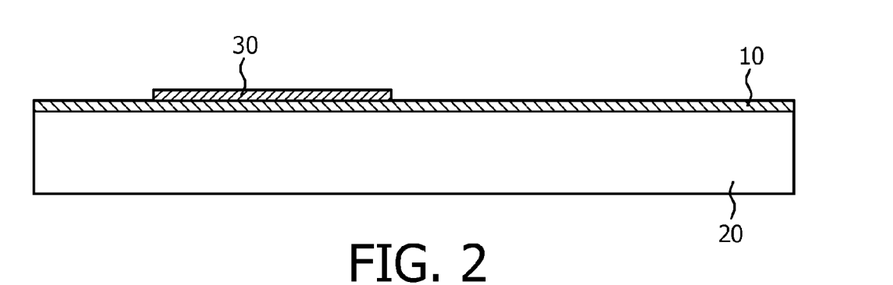

FIG. 2 shows the formation of an electrically driven thermal element such as a thermal resistor, e.g. deposition and patterning of 0.3 micron in-situ doped (n++) polysilicon layer 30 using a first mask: MASK 1:PS. Polysilicon layer 30 can be formed into one or more heating elements and/or one or more temperature sensing elements such as resistors, transistors or thermocouples. The heating element can be located separately and the polysilicon layer is only used a temperature sensing element. Where a heating element is provided this heats up the part of the fluid that is located close to the sensor. The fluid flow induces a decrease in the heater temperature, which can be measured with a temperature sensing element. Both the heater temperature as well as the shift in temperature of the temperature sensor can be used as a measure for the flow rate.

Figure 3:
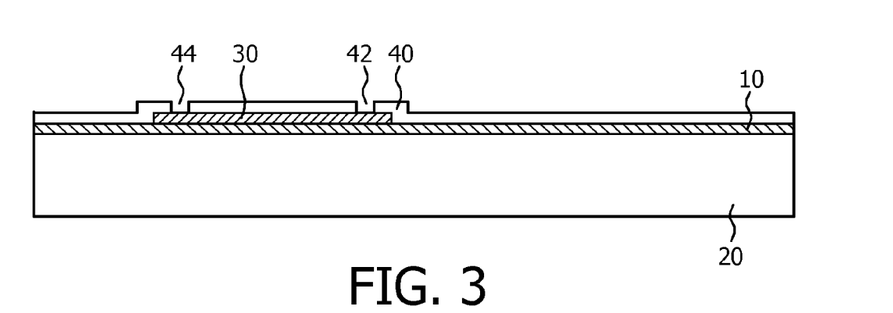
Figure 4:
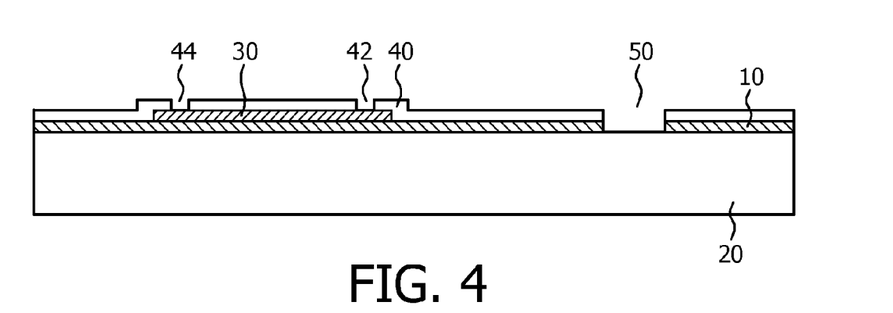
Figure 5:
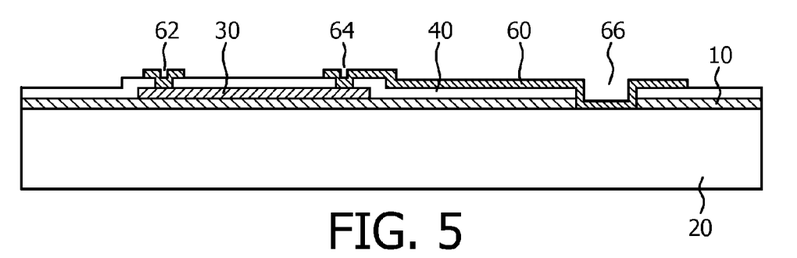

FIG. 3 shows formation of a pre-metal dielectric layer such as a 0.2 micron TEOS layer 40 and opening of first contact holes 42, 44 over the thermal element, e.g. polysilicon layer 30. This uses a second mask: MASK 2:CO. FIG. 4 shows the opening of second contact holes 50 to the substrate for bondpads. This can use a third mask: MASK 3: CB. In FIG. 5 is shown formation of a conductive layer that can be a metallization layer such as a metal stack, e.g. a 20 nm Ti+0.5 Aluminum metallization layer 60 to make electrical contact between the elements especially contacts 62, 64 to the thermal element made of polysilicon 30 through the first contact holes 42, 44 and the contact 66 to the bond pad hole or second contact hole 50. This can use a fourth mask: MASK 4:IN. The contacts 62, 64, 66 allow the electrical connections to drive the thermal element and to operate the sensor.

Figure 6:
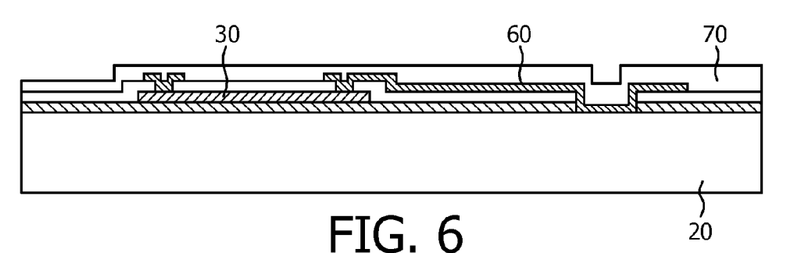
Figure 7:
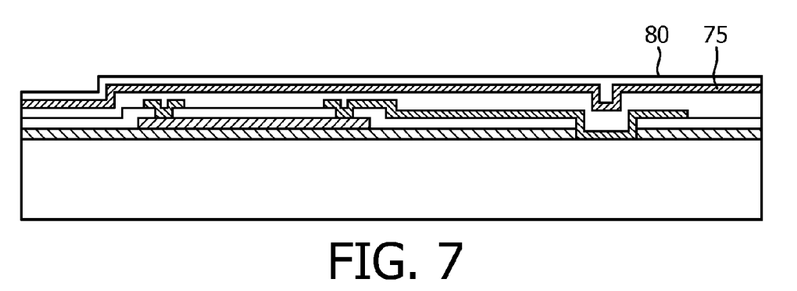

FIG. 6 shows forming a passivation layer and a scratch protection layer over the complete device such as forming a 0.5 micron PECVD nitride and 0.5 micron oxide layer 70 for passivation and scratch protection. The part of the sensor which will be closest to the fluid channel is above the polysilicon layer 30 so that further layers may be deposited to provide thermal conductance and to improve adhesion, e.g. FIG. 7 shows forming a metal layer such as a 0.05-1 micron aluminum layer 75 to tune thermal conductivity and an insulating layer such as a 0.5 micron oxide layer 80 for adhesion. To obtain optimal response time and sensitivity the average thermal conductance of the stack can be tuned by adapting the thickness of an additional (un-patterned) metallization layer.

Figure 8:
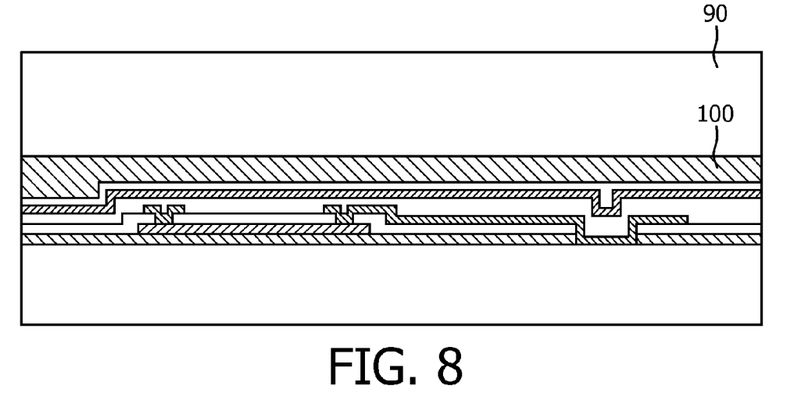
Figure 9:
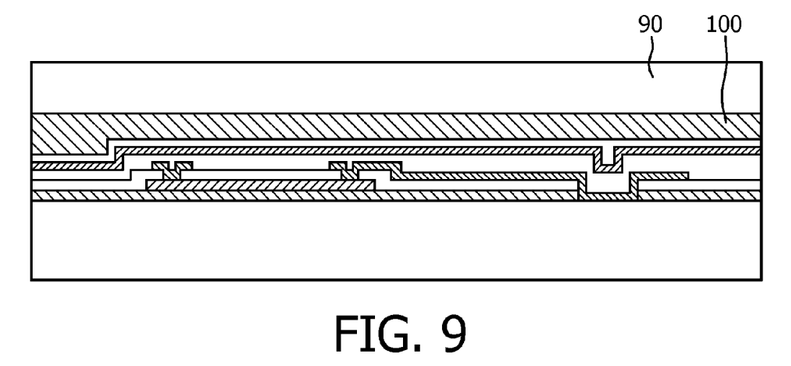

FIG. 8 shows a bonding process to a chemically resistant smooth and flat surface layer. For example, glue 100 is applied followed by an insulating substrate 90. The insulating substrate 90 may be manufactured from glass, which has a thermal conductivity of about 1 W/(mK). When manufactured from glass; the insulating substrate will typically have a thickness of about 400 micron. This can be implemented by placing the semiconductor wafer top down on the insulating substrate 90. Then the insulating substrate 90 is optionally thinned, e.g. by (DISCO-) grinding to a thickness of 50-100 micron followed by an optional polishing step to ensure a smooth sensor surface as shown in FIG. 9. Alternatively, the insulating substrate 90 is manufactured from poly-imide which has a thermal conductivity of about 0.15 W/(mK) and a thickness of roughly 10 micron. As a result, thermal shunting of the area in which the sensor is to be situated is reduced. This advantageously increases sensitivity of the sensor. Furthermore the smaller thickness positively affects the sensor's response time. In addition to that, poly-imide is easily applied on the semiconductor wafer, e.g. by spin-coating methodologies, which methodologies advantageously circumvents the need for gluing the insulating substrate 90.

Figure 10:
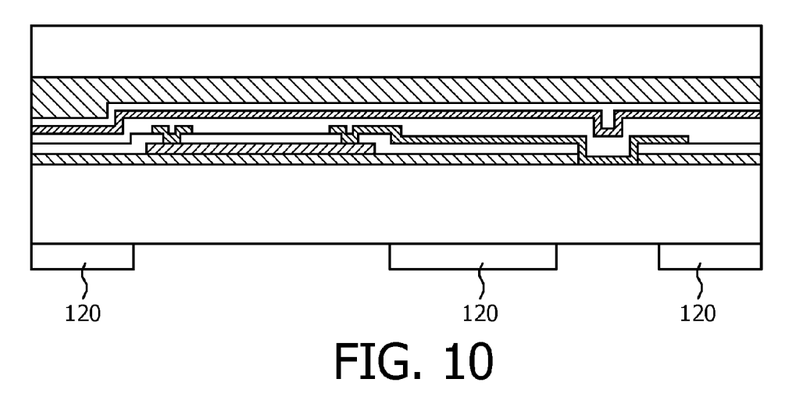

FIG. 10 shows forming a backside mask 120, e.g. a resist layer, for anisotropic etching such as deep RIE etching using a fifth mask: MASK 5:CAV.

Figure 11:
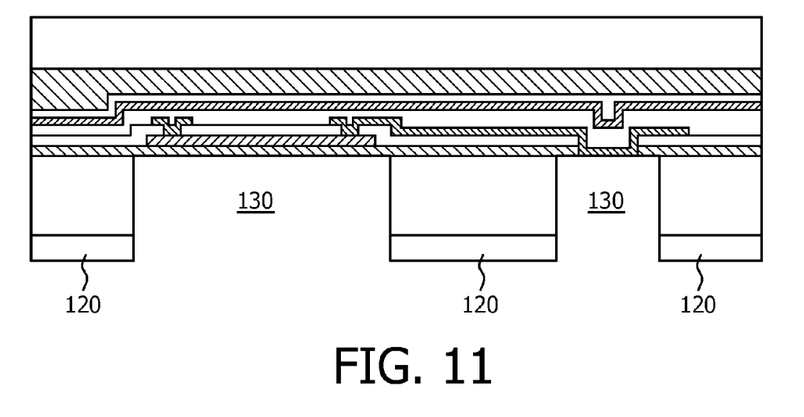

FIG. 11 shows forming the apertures 130 in the semiconductor substrate to open the bondpads by locally removing the semiconductor material, e.g. silicon. This can involve anisotropic etching such as a deep RIE etching (Bosch process) stopping on the insulating layer, e.g. oxide 10 and the conductive layer 60, e.g. metal, e.g. aluminum bondpads. Note that the aluminum bondpads are located directly on the silicon substrate so that removing the substrate opens the bond pad. Optionally, the silicon underneath the sensing area can be removed to increase the sensor sensitivity. The remaining silicon provides mechanical strength and functions as a heat sink. Now the sensor can be contacted e.g. using wirebonding.

Figure 12:
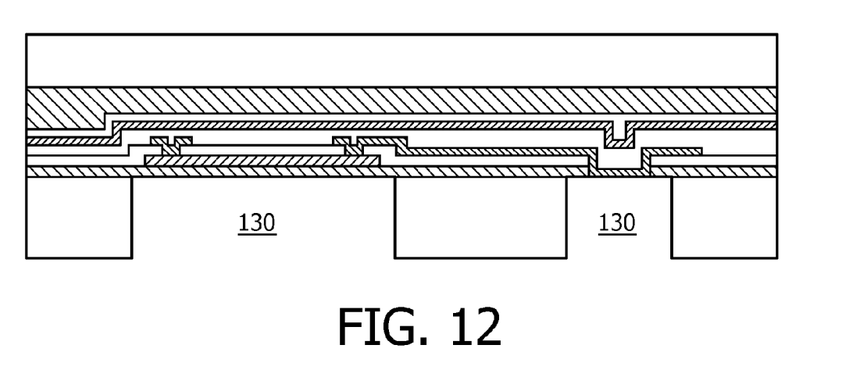
Figure 13:
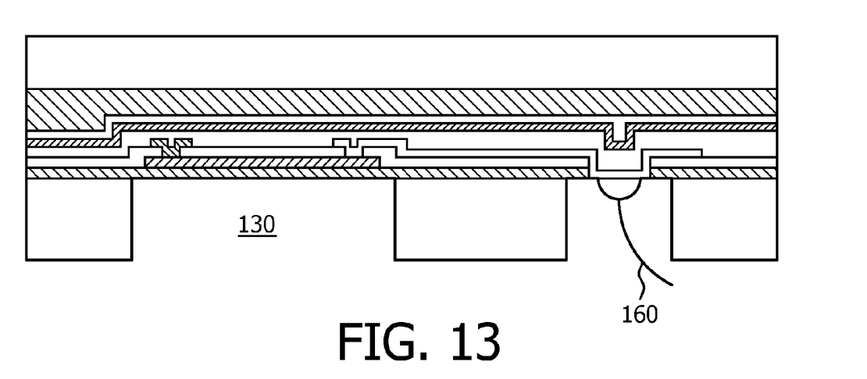

FIG. 12 shows removing the backside mask, e.g. resist layer 120. FIG. 13 shows a final step of dicing and providing a wirebond 160 to external circuitry such as a PCB or flexfoil.

A second embodiment involves fabricating electrically isolated semiconductor, e.g. silicon, 'pillars' to move the electrical connection of the sensor to the backplane of the stack. A starting material is for example a semiconductor wafer, e.g. a highly doped low resistive substrate with an insulating layer on top such as a thermal oxide layer on top. The heating elements and/or temperature sensing elements are processed using standard deposition and lithography techniques and are as shown in FIGS. 2 to 7 described in relation to the first embodiment, i.e. from the polysilicon layer 30. To obtain optimal response time and sensitivity the average thermal conductance of the stack can be tuned by adapting the thickness of an additional metallization layer as shown in FIG. 7. The wafer is bonded e.g. by gluing top down to a glass substrate as shown in FIG. 8, and the glass substrate is optionally thinned by (DISCO-) grinding to a thickness of 50-100 micron followed by a polish step to ensure a smooth sensor surface as shown in FIG. 9. In place of the method steps described with respect to FIGS. 10 to 13 of the first embodiment, the second embodiment has steps shown in FIGS. 14 to 19.

Figure 14:
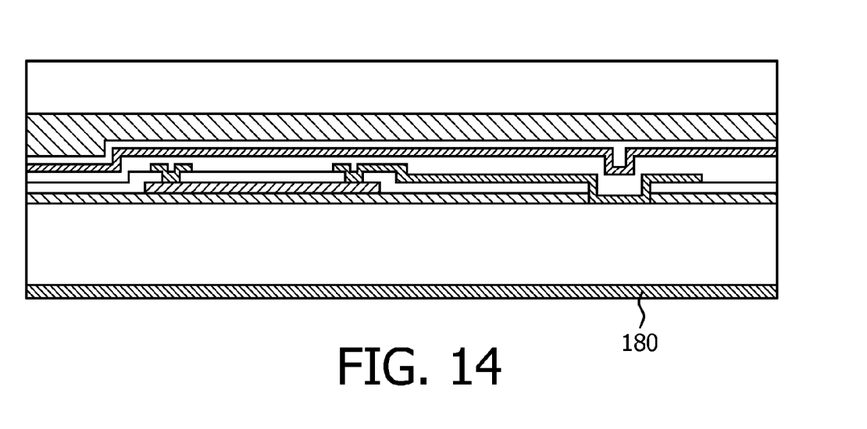
FIGS. 14 to 21 show steps in an alternative method of manufacturing an integrated circuit according to another embodiment, having the bond pad on a pillar on a backside of the substrate.
Figure 15:
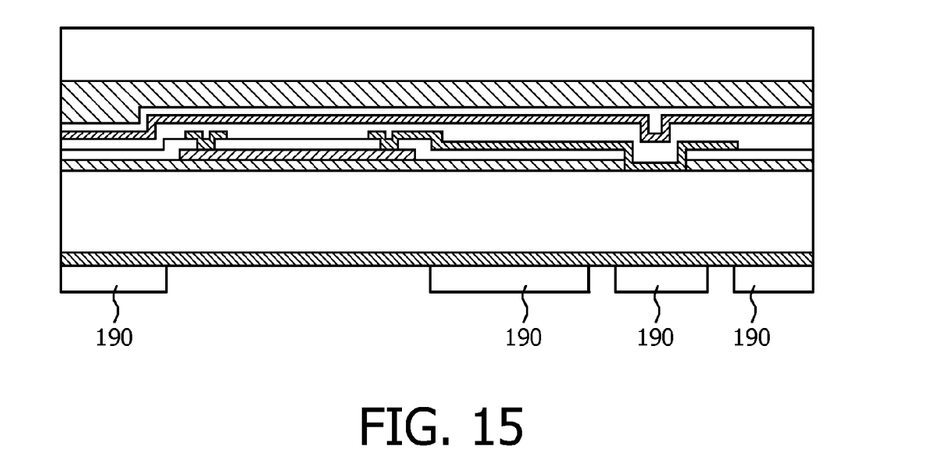
Figure 16:
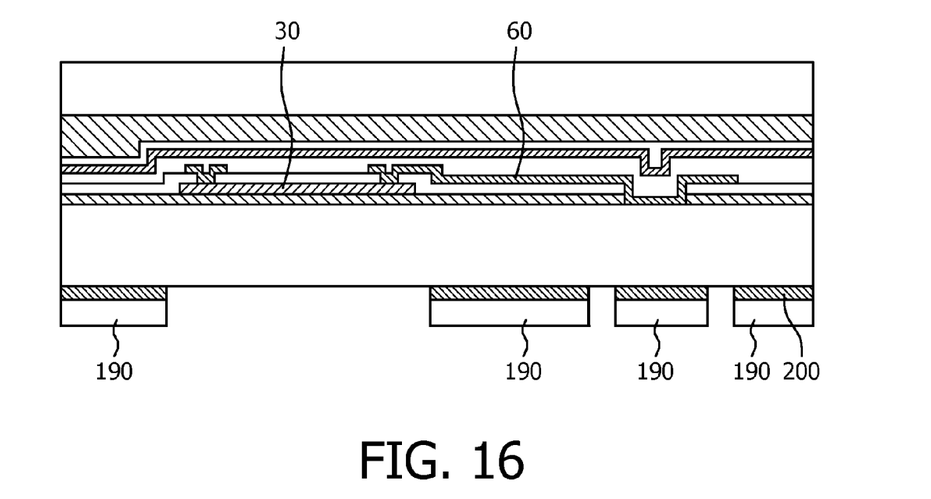

FIG. 14 shows the deposition of a metal layer such as a 0.5 micron aluminum layer 180 on a backside of the wafer for example by sputtering. FIG. 15 shows a backside mask for anisotropic etching, e.g. deep RIE etching: MASK 5:CAV. This can be a resist layer 190. This is used to pattern the metal layer, e.g. aluminum layer 180 to define the bond pads 200 as shown in FIG. 16.

Figure 17:
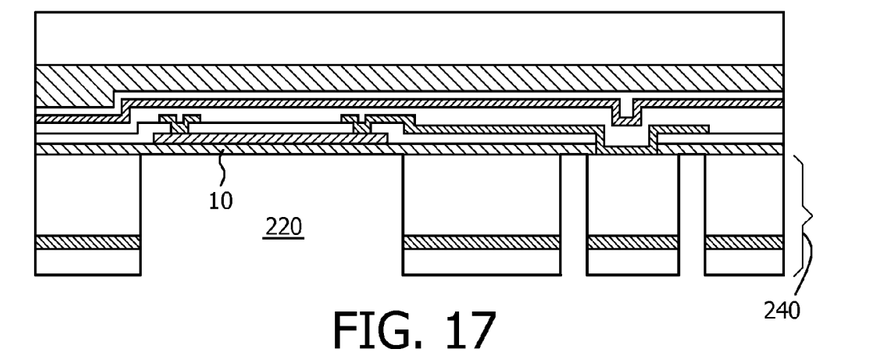

FIG. 17 shows anisotropic etching, e.g. deep RIE etching (Bosch process) stopping on the oxide layer 10 (and any aluminum layer 60). This enables the silicon 220 underneath the sensing area to be removed to increase the sensor sensitivity, and the silicon around the bondpads is removed to form electrically isolated silicon 'pillars' 240 providing an electrical connection between the sensor and the bondpads. The remaining silicon provides mechanical strength and functions as a heat sink for the sensor. Now the sensor can be contacted e.g. using wirebonding.

Figure 18:
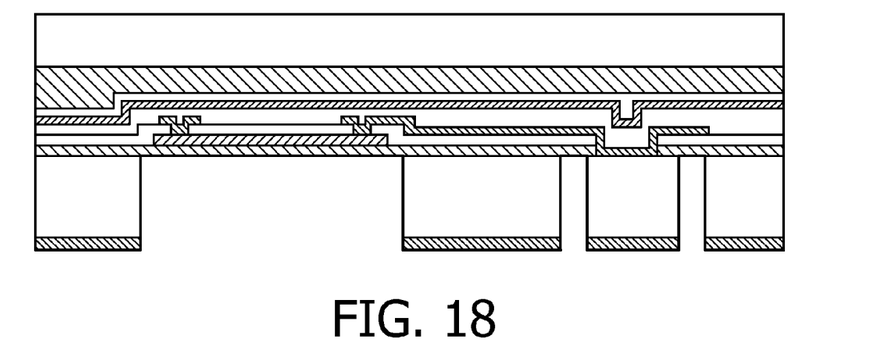

FIG. 18 shows removing the resist layer.

Figure 19:
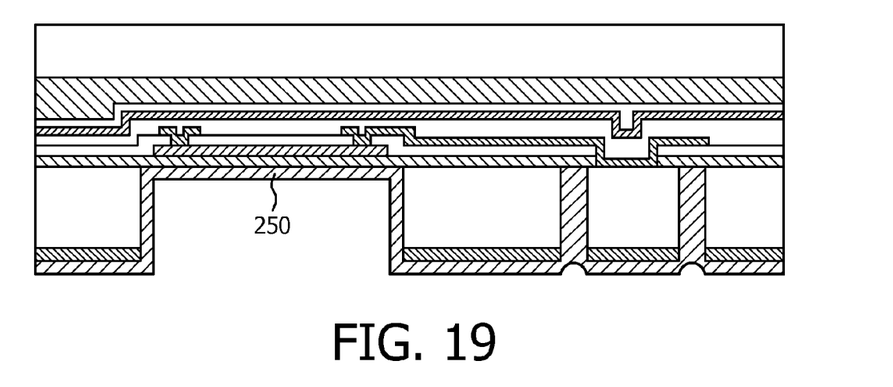

FIG. 19 depicts providing a coating 250 of electrical resistive material at the backside of the stack. Herein the trenches between the pillars 240 are filled with the coating 250. Also the remaining silicon substrate is provided with the coating 250 of electrical resistive material. Preferably, the coating 250 comprises parylene. The coating 250 has a thickness such that trenches between the pillars are completely filled, i.e. the coating 250 has a thickness that equals roughly half the width of the trenches between the pillars 240.

Figure 20:
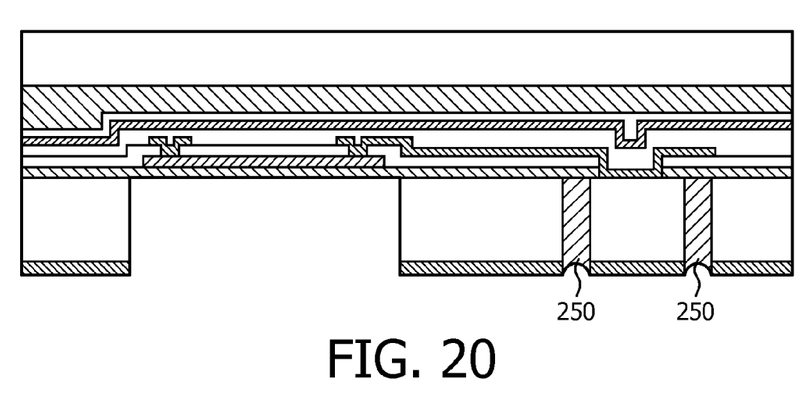

FIG. 20 displays removing the coating 250 by way of applying an oxygen plasma to it until all coating 250 is removed from the oxide layer 10 and the pillar's top surfaces.

Only a small fraction will be removed of the coating 250 deposited in the trenches between the pillars 240, this fraction will have a thickness that is more or less equal to the original thickness of the coating 250.

Figure 21:
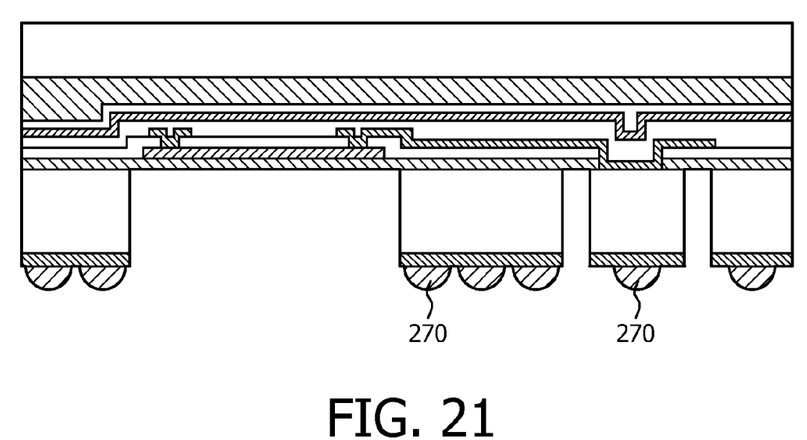

FIG. 21 shows wafer-scale processing to form stud bumps 270. This can be followed by dicing of the wafer to provide individual integrated circuits.

A third embodiment involves fabricating the sensors of embodiments 1 and 2 using the same steps as described above but the starting material is an SOI (silicon-on-insulator) wafer having a mono-crystalline upper layer above an insulating layer. In this embodiment driving electronics such as A/D converters etc. can be processed in the mono-crystalline silicon layer of the SOI. Also the temperature sensing elements can be processed in the mono-crystalline silicon instead of using a separate polysilicon layer 30.

Figure 22:
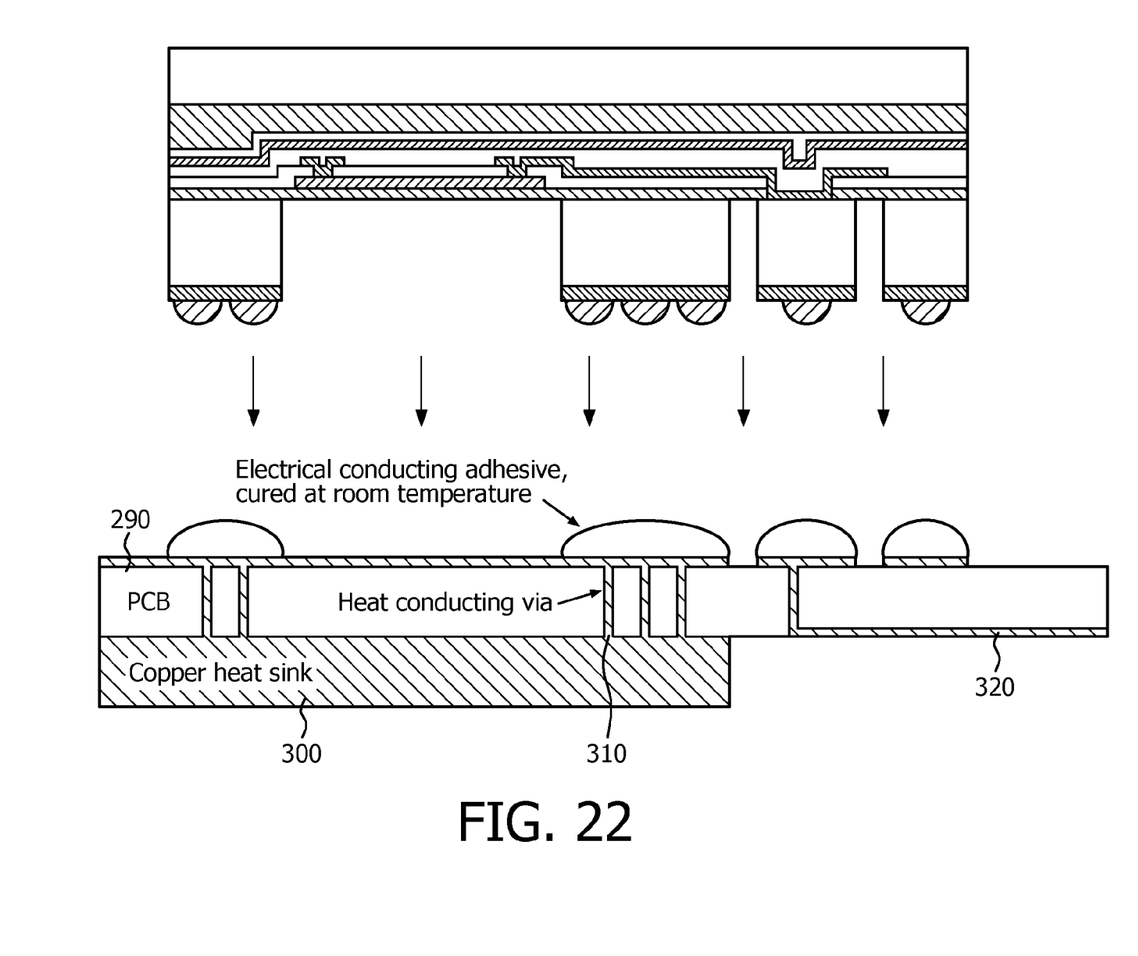
FIG. 22 shows forming an assembly by mounting the integrated circuit on a PCB.
Figure 23:
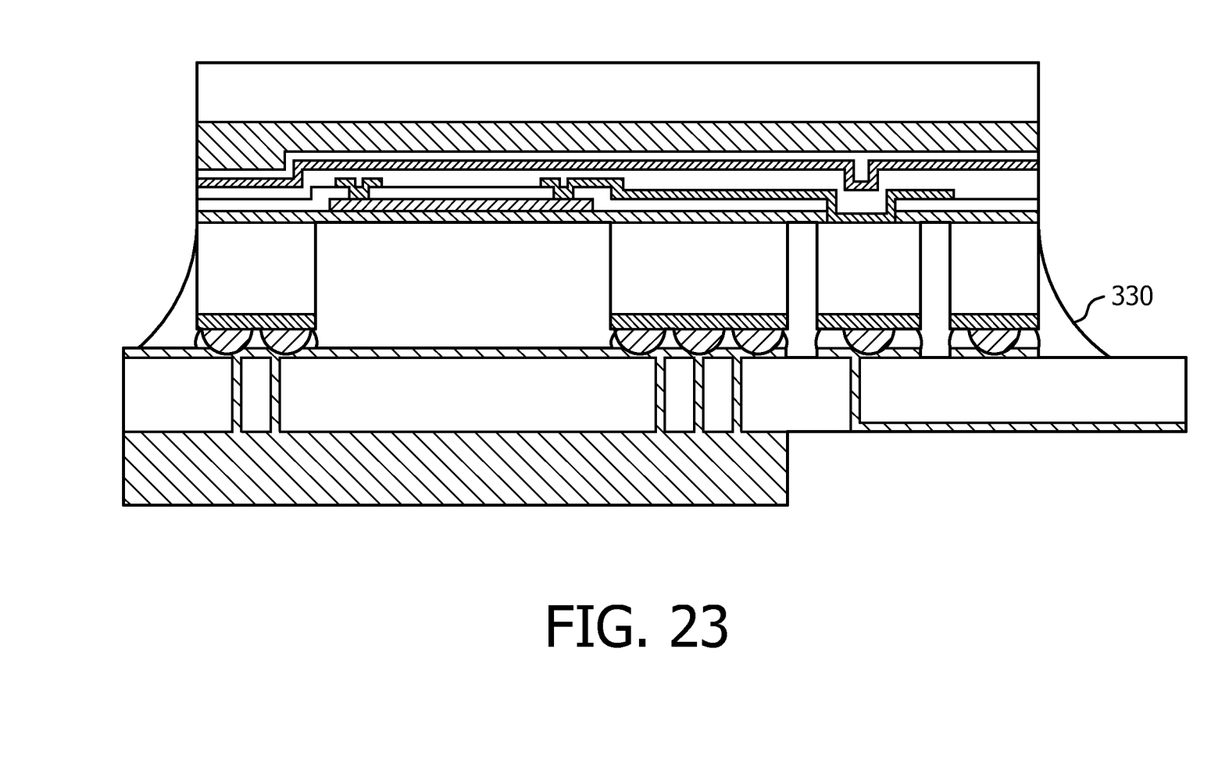
FIG. 23 shows applying sealant to the assembly.

In a fourth embodiment a method to mount the sensor stack as described in any of the embodiments is presented. As an example the sensor device as in the second embodiment is mounted directly on a PCB as shown in FIGS. 22 and 23. Stud bumps are applied on the bond pads to provide a good electrical connection to the PCB 290. Additionally, stud bumps are applied underneath the silicon heat sink to provide a good thermal connection to the PCB. Electrical conductive adhesive 280 is applied on the PCB. The adhesive should be chosen to reduce the mismatch of the thermal expansion coefficients of the silicon and the PCB. Preferably a conductive epoxy that is cured at room temperature is used to prevent introduction of stress in the sensor due to a mismatch of the thermal expansion coefficients of the silicon and the PCB. To avoid penetration of water (vapor) and dirt into the gap between the sensor and the PCB an adhesive 330 is applied to seal the sensor. A heat sink 300 can be mounted at the backside of the PCB and connected with the silicon heat sink by thermally conductive vias 310 through the PCB. Electrical connections 320 are shown for coupling the bond pads of the sensor to other components on the PCB. These connections can include conventional vias and printed copper lines.

Figure 24:
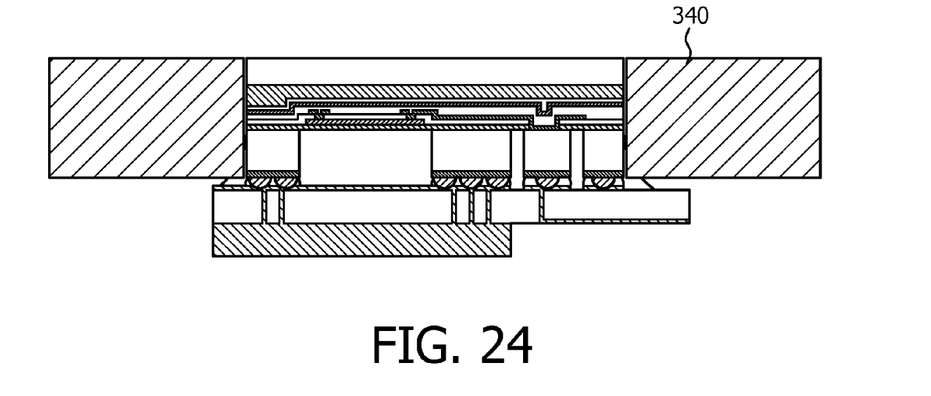
FIGS. 24 and 25 show the assembly mounted in a channel wall according to alternative embodiments.
Figure 25:
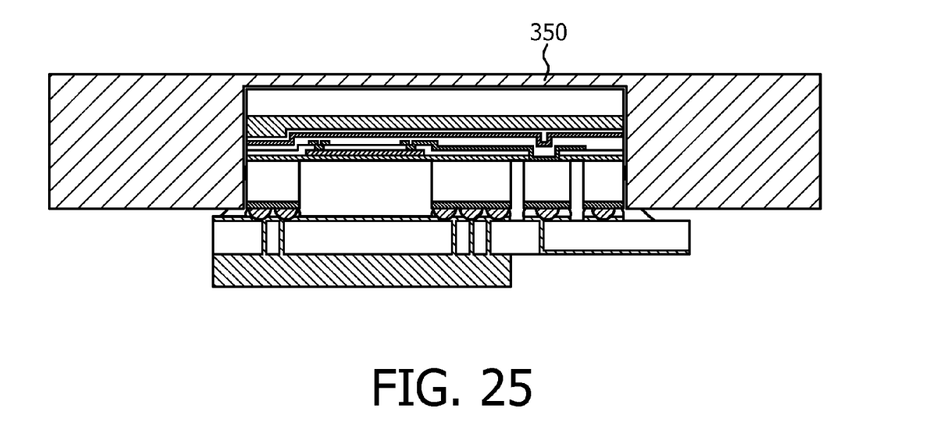

FIG. 24 shows the mounting of the assembly having the flow sensor according to any of the embodiments of the present invention in a recess in the form of a prefabricated window in the flow channel wall 340. In this view the flow channel is above the sensor. FIG. 25 shows the mounting of the flow sensor behind an alternative type of recess in the form of a locally thinned part 350 of the flow channel wall. This thinned part can provide a barrier to reduce a risk of leakage or contamination of the fluid, and avoid a need to provide a good seal around the edges of the sensor integrated circuit.

The sensors, assemblies and fabrication methods are not restricted to be applied in nebuliser systems. They can be applied in other medical applications where sterility is required such as in IV infusion drug delivery. Also they can be applied in applications other than medical fields, e.g. for use in environments with aggressive fluids.

In embodiments of thermal flow sensors, the sensor is located on top or in the upper layer of a silicon substrate. Conventionally both the sensor area and the bond pads to connect the sensor with e.g. driving electronics located at the front side of the silicon stack. In such conventional devices the sensor area and the bond pads are located in a same plane, so that when embedding the thermal flow sensor in the wall of a tubing, it is necessary to apply a thick layer between the sensor and the fluid flowing though the tubing in order to provide room and to protect and guide the connecting wires to a PCB or lead frame. The embodiments of the present invention described can address this problem which can affect the performance of the sensor in terms of sensitivity and response time. Decreasing the distance between the temperature sensing elements comprised in the thermal sensor and the fluid flowing through the fluid channel by the embodiments described above can improve response time and sensitivity of the sensor.

Other variations and applications can be envisaged within the claims.

The invention claimed is:

1. A thermal flow sensor device for sensing a flow in a fluid channel based on temperature measurements, the device comprising:
   an electrically driven thermal element on a front side of the thermal flow sensor device arranged to face the channel,
   a bond pad coupled electrically through physical contact with a channel facing side of the electrically driven thermal element and configured to facilitate electrical contact with a printed circuit board of the thermal flow sensor device via a surface of the bond pad that faces away from the channel and is accessible for electrical contact with the printed circuit board of the thermal flow sensor device; and
   a substrate, the substrate being patterned to provide apertures to expose the bond pad and increase sensitivity of the electrically driven thermal element such that a location of the physical contact between the bond pad and the electrically driven thermal element corresponds to a first aperture in the substrate and electrical contact between the bond pad and the printed circuit board is made via a second aperture in the substrate.

2. The thermal flow sensor device according to claim 1, comprising a conductive layer on the front side of the thermal flow sensor device, for electrical connection between the electrically driven thermal element and the bond pad, the bond pad being located at a back side of the conductive layer, the back side of the conductive layer facing away from the channel.

3. The thermal flow sensor device according to claim 1, comprising an insulating layer for electrically insulating the thermal flow sensor device from a fluid in the channel.

4. The thermal flow sensor device according to claim 3, wherein the insulating layer comprises poly-imide.

5. The thermal flow sensor device according to claim 1, the electrically driven thermal element being located at a front side of the substrate facing the channel, the substrate being patterned to form one or more pillars on a back side of the substrate, the bond pad being located on the back side of the substrate on one of the pillars.

6. The thermal flow sensor device according to claim 5, wherein the one or more pillars are provided with a coating of electrical resistive material.

7. The thermal flow sensor device according to claim 6, wherein the coating comprises parylene.

8. The thermal flow sensor device according to claim 1, wherein the electrically driven thermal element comprises a heating element or a temperature sensor element on the front side of the thermal flow sensor device facing the channel.

9. The thermal flow sensor device according to claim 8 wherein the heating element is formed as a resistor.

10. The thermal flow sensor device according to claim 9 wherein the resistor is made of polysilicon.

11. The thermal flow sensor device according to claim 1, wherein the thermal flow sensor device is formed as an integrated circuit.

12. The thermal flow sensor device according to claim 1, formed as a silicon on insulator integrated circuit.

13. The thermal flow sensor device according to claim 1, wherein the thermal flow sensor device is mounted on the printed circuit board, with the bond pad coupled to a corresponding contact on the printed circuit board.

14. The thermal flow sensor device according to claim 1, wherein the thermal flow sensor device is mounted in a recess in a wall of the channel such that the electrically driven thermal element faces the channel.

15. The thermal flow sensor device according to claim 1, wherein the thermal flow sensor device is included in a nebulizer system.

\* \* \* \* \*